United States Patent [19]

Jones et al.

[11] Patent Number: 5,217,902
[45] Date of Patent: Jun. 8, 1993

[54] METHOD OF INTRODUCING SPECTINOMYCIN RESISTANCE INTO PLANTS

[75] Inventors: Jonathan Jones, Norwich, United Kingdom; Pal Maliga, East Brunswick, N.J.

[73] Assignee: DNA Plant Technology Corporation, Oakland, Calif.

[21] Appl. No.: 709,537

[22] Filed: Jun. 3, 1991

Related U.S. Application Data

[62] Division of Ser. No. 357,493, May 26, 1989, Pat. No. 5,073,675.

[51] Int. Cl.$^5$ .................. C12N 15/54; C12N 15/82
[52] U.S. Cl. .................. 435/320.1; 435/15; 435/172.3; 800/205
[58] Field of Search ........... 536/27; 435/320.1, 240.4, 435/172.3, 15; 800/205; 935/30

[56] References Cited

PUBLICATIONS

Chinault, et al (1986) Plasmid 15: 119-131.
Rogers, et al. in Methods in Enzymology 153, Academic Press, NY, 1987, pp. 253-277.
Hayford, M. B., et al., "Development of a Plant Transformation Selection System Based on Expression of Genes Encoding Gentamicin Acetyltransferases," *Plant Physiol.*, 86:1216-1222 (1987).
Bevan, M. W., et al., "A chimaeric antibiotic resistance gene as a selectable marker for plant cell transformation," *Nature*, 304:184-187 (1983).
Rothstein, S. J., et al., "Promoter cassettes, antibiotic-resistance genes, and vectors for plant transformation," *Gene*, 53:153-161 (1987).
Eichholtz, D. A., et al., "Expression of Mouse Dihydrofolate Reductase Gene Confers Methotrexate Resistance in Transgenic Petunia Plants," *Somatic Cell and Molecular Genetics*, 13:67-76 (1987).
Jones, J. D. G., et al., "A dominant nuclear streptomycin resistance marker for plant cell transformation," *Mol. Gen. Genet.*, 210:86-91 (1987).
Maliga, P., et al., "Improved expression of streptomycin resistance in plants due to a deletion in the streptomycin phosphotransferase coding sequence," *Mol. Gen. Genet.*, 214:456-459 (1988).
Fromm, H., et al., "The molecular basis for rRNA-dependent spectinomycin resistance in Nicotiana chloroplasts," *EMBO*, 6:3233-3237 (1987).
Uchimiya, H., et al., "Co-expression and inheritance of foreign genes in transformants obtained by direct DNA transformation of tobacco protoplasts," *Mol Gen Genet*, 205:1-8 (1986).
Fraley, Robert T., et al., "Expression of bacterial genes in plant cells," *Proc. Natl. Acad. Sci., USA*, 80:4803-4807 (1983).
Ellis, R. John, "Molecular Chaperones: The Plant Connection," *Science*, 250:954-958 (16 Nov. 1990).
Weising, Kurt, et al., "Foreign Genes in Plants: Transfer, Structure, Expression, and Applications," *Annu. Rev. Genet.* 22:421-477 (1980).
Comai, L., et al., "Expression in plants of a mutant aroA gene from Salmonella typhimurium confers tolerance to glyphosate," *Nature* 317:741-744 (24 Oct. 1985).
Lund, Peter, et al., "Bacterial Chitinase Is Modified and Secreted in Transgenic Tobacco," *Plant Physiol.* 91:130-135 (1989).

(List continued on next page.)

Primary Examiner—Che S. Chereskin
Attorney, Agent, or Firm—Clinton H. Neagley

[57] ABSTRACT

This invention relates to the discovery that the prokaryotic enzyme, aminoglycoside 3''-adenyltransferase (AGAT), in particular as encoded by a bacterial aadA gene, is useful as a selectable marker for transformed plants. The enzyme conveys resistance to spectinomycin and streptomycin. Such markers are particularly advantageous because they are non-lethal, provide rapid visual identification of transformed cells and permit selection in media containing either spectinomycin or streptomycin. In addition, AGAT may be used as a selectable marker which differentiates by enabling survival on selective media.

2 Claims, 1 Drawing Sheet

OTHER PUBLICATIONS

Vaeck, Mark, et al., "Transgenic plants protected from insect attack," *Nature* 328:33-37 (2 Jul. 1987).

Amasino, Richard M., et al., "Changes in T-DNA methylation and expression are associated with phenotypic variation and plant regeneration in a crown gall tumor line," *Mol. Gen. Genet.* 197:437-446 (1984).

Hepburn, A. G., et al., "The role of Cytosine Methylation in the Control of Nopaline Synthase Gene Expression in a Plant Tumor," *J. Mol. Appl. Genet.* 2(3):315-329 (1983).

Rogers, S. G., et al., "Improved vectors for plant transformation: Expression cassette vectors and new selectable markers," in *Methods in Enzymology*, vol. 153, pp. 253-277, Academic Press, N.Y. (1987).

Potrykus, I., "Gene transfer to cereals: An assessment," *Bio/Technology*, 8:535-542 (Jun. 1990).

Svab, Z., et al., "Aminoglycoside-3"-adenyltransferase confers resistance to spectinomycin streptomycin in *Nicotiana tabacum*," *Plant Molecular Biology*, 14:197-205 (1990).

METHOD OF INTRODUCING SPECTINOMYCIN RESISTANCE INTO PLANTS

This is a division of application Ser. No. 07/357,493, filed May 26, 1989, now U.S. Pat. No. 5,073,675.

BACKGROUND OF THE INVENTION

Field of the Invention

This invention relates to the discovery that the prokaryotic enzyme, aminoglycoside 3″-adenyltransferase (AGAT), in particular as encoded by a bacterial aadA gene, is useful as a selectable marker for transformed plants. The enzyme conveys resistance to spectinomycin and streptomycin. Such markers are particularly advantageous because they are non-lethal, provide rapid visual identification of transformed cells and permit selection in media containing either spectinomycin or streptomycin. In addition, AGAT may be used as a selectable marker which differentiates by enabling survival on selective media.

Specifically, this invention discloses vectors for transforming the plants with the prokaryotic transferase, plants containing the transferase and methods for selecting plants transformed with vectors having DNA sequences encoding bacterial adenyl transferases.

Information Disclosure

Bacterial resistance to spectinomycin and streptomycin based upon aminoglycoside, 3″-adenyltransferase is known. Chinault, A.C., 1986, Plasmid 15, 119-131, 1986.

Bacterial genes for resistance to antibiotics have been expressed in plants, including kanamycin, Bevan, et al., Nature, 304:184-187, 1983, and Fraley, et al., Proc. Nat'l. Acad. Sci., USA, 80, 4803-4807, 1983; hygromycin, Rothstein, et al., Gene, 53:153-161, 1987; methotrexate, Eicholtz, et al., Somatic Cell and Molecular Genetics, 13:67-76, 1987; gentamicin, Hayford, et al., Plant Physiol., 86, 1216-1223, 1987; and streptomycin, Jones, et al., Mol. Gen. Genet., 210 (1):86-91, 1987, and Maliga, P., et al., Mol. Gen. Genet., 214 (3):456-459, 1988.

Spectinomymcin resistance conferred by mutations in the plastid rDNA gene in higher plants is known. Fromm, H., et al., EMBO J, 6:3233-3237, 1987.

SUMMARY OF THE INVENTION

This invention provides for a DNA sequence conveying spectinomycin resistance in plants and comprises a recombinant expression cassette containing a DNA sequence encoding an aminoglycoside 3″-adenyltransferase (AGAT). The gene encoding AGAT is typically from a prokaryote and is preferably from a Shigella species of bacteria. A preferred recombinant construct comprises an expression cassette having a promoter selected from the group comprising plant viral promoters and the 2′ gene of the T-DNA of Agrobacterium tumefaciens. Plants transformed with the above DNA sequence and progeny of such plants are also disclosed herein.

Finally there are disclosed herein, methods for selecting transformed plants comprising the steps of transforming the plants with the above described DNA sequence; cultivating the transformed plants and selecting transformed plants expressing aminoglycoside 3″-adenyltransferase. More specifically, this method involves the selection of transformed plants by cultivation on a medium comprising spectinomycin, streptomycin or combinations thereof.

DETAILED DESCRIPTION OF THE PREFERRED EMBODIMENT

Figure 1:
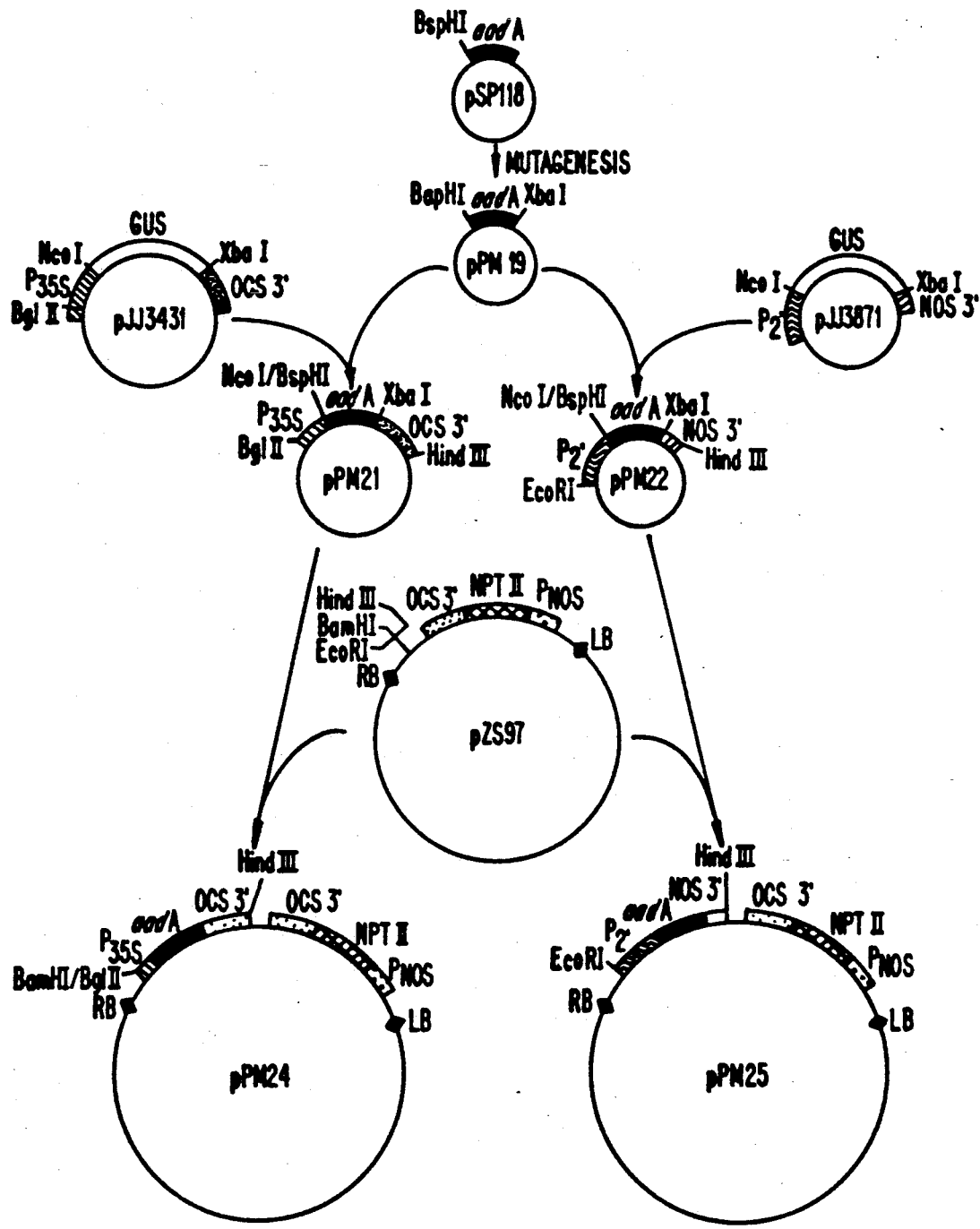
FIG. 1 illustrates a construction of chimeric aadA genes for expression in plants.

This invention relates to a means for selecting plants that have been transformed with a genetically engineered DNA sequence. This invention particularly relates to the production and use of plant cells transformed by recombinant genetic techniques to express resistance to streptomycin and spectinomycin. This resistance is expressed through the heterologous production of a bacterial aminoglycoside 3″-adenyltransferase by transformed plant cells whose genomes incorporate these genes.

Unlike bacterial cells which multiply rapidly and are readily selectable using a variety of markers, the selection of transformed plant cells growing in culture is more difficult. Selection of transformed plants is typically achieved by assaying for resistance to toxic substances in the growth medium. Genes responsible for such resistance are known and have been incorporated into plant genomes in several examples.

Currently available markers for plants are limited in number and most rely on killing cells for selectivity. Prior to this work, streptomycin resistance based upon the streptomycin phosphotransferase (SPT) gene was the most readily available non-lethal resistance marker for use in transgenic plants. Expression of the SPT gene results in color differentiation in both tissue culture and seedlings evidenced by the bleaching of sensitive cells in the presence of the antibiotic. This screening assay, however, is inoperable in some species.

The AGAT enzyme allows green coloration in plant tissue grown on growth medium containing spectinomycin or streptomycin. Expression of the AGAT enzyme also provides a non-lethal selectable marker. Unlike the phosphotransferase gene, the adenyltransferase gene is able to confer resistance to both streptomycin and spectinomycin.

Furthermore, there are situations where alternative second markers are desirable. For example, when attempting to transform cells with multiple heterologous genes, it is helpful to monitor transformation of each gene with a unique marker. Moreover, the system is valuable because it can be used in many situations, i.e., for plants normally sensitive to either one or both antibiotics.

Thus, it is the objective of the disclosed recombinant systems to provide an easily-assayed, color-differentiated, non-lethal means to determine resistance to streptomycin and to spectinomycin in plants using bacterial adenytransferases. It should be noted that in cells which are particularly sensitive to spectinomycin or streptomycin or if these antibiotics are applied at concentrations in excess of that required for color differential such that cell death occurs, resistance to spectinomycin can be used as a selective marker in a similar manner to kanamycin or hygromycin resistance.

Accordingly, the method of the invention permits selection of transformed plants where selection is based on non-lethal color differentiation (e.g., bleaching versus green color), non-lethal differential growth rate or non-lethal differential fitness. The method also permits selection based on lethality. An advantage of non-lethal selection is the avoidance of limitations associated with maintaining cells in an environment ("cell death environment") where other cells are dead or dying.

To facilitate the production of the enzyme and the transformation of plant cells producing it, one utilizes recombinant DNA techniques to introduce a gene encoding aminoglycoside 3"-adenyltransferse into a suitable cloning vector which is subsequently propagated in a suitable host cell. In the exemplified case, *Agrobacterium tumefaciens* is used as a vehicle for transmission of the gene to the ultimate host, the tobacco cell, wherein the plant is induced to express and produce the active enzyme.

The following descriptions will detail various methods available to express genes encoding aminoglycoside 3"-adenyltransferase in plant cells, and is followed by specific examples of preferred methods.

In summary, the manipulations can be described as 1) obtention of the gene encoding AGAT from its natural host, 2) fusing to a promoter which directs expression of the gene in plant cells and 3) the expression of the gene in suitable plant host cells. The desired transformed cells are then selected, preferably on the basis of their visual appearance, under appropriate culture conditions.

A. General Methods

Generally, the nomenclature and general laboratory procedures with respect to recombinant DNA technology can be found in Maniatis, T. et al., *Molecular Cloning—A Laboratory Manual*, Cold Spring Harbor Laboratory, Cold Spring Harbor, N.Y., 1985. The manual is hereinafter referred to as "Maniatis". Other general references are provided throughout this document. The procedures therein are believed to be well known in the art and are provided for the convenience of the reader. All the information contained therein is incorporated herein by references.

B. Sources of genes encoding aminoglycoside 3"-adenyltransferase (AGAT)

By selecting bacterial cultures which are resistant to both spectinomycin and streptomycin, one can obtain a natural source of the gene useful in this invention. The most ready source of AGAT are from clinical samples of Shigella species such as flexneri.

A description of a useful procedure for obtaining naturally occuring genes encoding adenyl transferase enzymes can be found in Chinault, et al., Plasmid 15,119- 131, 1986. Clinical bacterial cultures exhibiting the desired range of antibiotic resistance are cultured and further analyzed for adenyl transferase activity according to *Methods of Enzymology*, Vol. 43, 1975. In addition, transposon Tn7 carries a gene which confers spectinomycin and streptomycin resistance, Brevet, et al., *Mol. Gen. Genet.*, 201, 258-264, 1985, and is likely to be found in a variety of bacterial genera merely by using spectinomycin as a selective component in a growth medium.

Bacterial cultures having the requisite enzyme activity are further analyzed to localize the resistance gene encoding the transferase activity. This involves the use of standard methods for subcloning large uncharacterized regions of DNA. The entire bacterial DNA is first cloned in suitable plasmid vectors and the clones are then screened in bacteria for the transferase activity.

Once the gene is localized to a 1-2 kilobase fragment, sequence analysis can be done to confirm the identity of the gene and to provide information for later recombinant manipulations.

Genes encoding resistance to streptomycin and spectomycin have been previously described on bacterial plasmids (see S. Hollingshead and D. Vapnek, Plasmid, 13, 17-30, 1985; and A. Chinualt, et al., Plasmid 15, 119-131, 1986.

In addition, FIG. 7 of Plasmid 15, 119-131 provides the nucleotide sequence of the transferase gene used in the Examples and oligonucleotide probes can be derived from the sequence. These probes could be used to faciliate the identification of alternative sources of adenyl-transferase genes using genomic libraries derived from appropriately resistant bacterial cultures.

The transferase gene can be maintained in a replication vector until transformation into a suitable plant host.

C. Expression of aminoglycoside 3"-adenyltransferase in a plant hose

1. Vector construction

The desired vector construct will provide a AGAT expression cassette designed for plants and companion sequences upstream and downstream from the expression cassette. The companion sequences will be of plasmid or viral origin and provide necessary characteristics to the vector to permit the vectors to move DNA from bacteria to the desired plant host.

The basic bacterial/plant vector construct will preferably provide a broad host range prokaryote replication origin; a prokaryote selectable marker; and, for Agrobacterium transformations, T DNA sequences for Agrobacterium-mediated transfer to plant chromosomes.

Suitable prokaryote selectable markers include resistance toward antibiotics such as kanamycin or tetracycline. Other DNA sequences encoding additional functions may also be present in the vector, as in known in the art.

The recombinant expression cassette will contain in addition to the AGAT encoding sequence, a promoter region, plant 5' untranslated sequences, initiation codon depending on whether or not the structural gene comes equipped with one, and a transcription and translation termination sequence. Unique restriction enzyme sites at the 5' and 3' ends of the cassette allow for easy insertion into a pre-existing vector.

Promoters to direct m-RNA transcription should operate effectively in plant hosts. One such promoter is the nos promoter from native Ti plasmids, Herrera-Estrella et al., *Nature* 303:209-213, 1983. Others include the 35S and 19S promoters of cauliflower mosaic virus, Odell et al., *Nature* 313:810-812, 1985, and the 2' promoter, Velten, et al., *EMBO J.* 3, 2723-2730, 1984.

Transcription enhancers are elements upstream from the promoter site and include the "TATA box" as well as less characterized sequences which vary from species to species, Ha and An, *Proc Nat. Acad. Sci.* 85:8017-8021, 1988.

Polyadenylation tails, Alber and Kawasaki, 1982, *Mol. and Appl. Genet.* 1:419-434 are also commonly added to the vector construct to optimize high levels of transcription and proper transcription termination, respectively. Polyadenylation sequences include but are not limited to the *Agrobacterium* octopine synthetase signal, Gielen et al., *EMBO J.* 3:835-846, 1984 or the nopaline synthase of the same species Depicker et al., *Mol. Appl. Genet.* 1:561-573, 1982.

The utility of this invention is to provide a means to detect transformed plant cells. An objective of such work is to express heterologous genes and thus the DNA sequences will typically contain at least one additional recombinant expression cassette comprising the components similar to the AGAT expression cassette described above.

Since the ultimate expression of the desired gene product will be in a eucaryotic cell (e.g., tobacco), it is desirable to determine whether any portion of the cloned gene contains sequences which will be processed out as introns by the host's splicosome machinery. If so, site-directed mutagenesis of the "intron" region may be conducted to prevent losing a portion of the genetic message as a false intron code, Reed and Maniatis, *Cell* 41:95-105, 1985.

2. Transformation of plant cells a. Direct Transformation

The AGAT vector can be microinjected directly into plant cells by use of micropipettes to mechanically transfer the recombinant DNA. Crossway, *Mol. Gen. Genetics*, 202:179-185, 1985. The genetic material may also be transferred into the plant cell by using polyethylene glycol, Krens, et al., *Nature*, 296, 72-74, 1982.

Another method of introduction of nucleic acid segments is high velocity ballistic penetration by small particles with the nucleic acid either within the matrix of small beads or particles, or on the surface, Klein, et al., *Nature*, 327, 70-73, 1987.

Yet another method of introduction would be fusion of protoplasts with other entities, either minicells, cells, lysosomes or other fusible lipid-surfaced bodies, Fraley, et al., *Proc. Natl. Acad. Sci. USA*, 79, 1859-1863, 1982.

The gene encoding AGAT may also be introduced into the plant cells by electroporation. (Fromm et al., *Pro. Natl Acad. Sci. USA* 82:5825, 1985). In this technique, plant protoplasts are elctroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

b. Vectored Transformation

Cauliflower mosaic virus (CaMV) may be used as a vector for introducing the gene encoding AGAT into plant cells. (Hohn et al., 1982 "*Molecular Biology of Plant Tumors,*" Academic Press, N.Y. pp. 549-560; Howell, U.S. Pat. No. 4,407,956). In accordance with the described method, the entire CaMV viral DNA genome is inserted into a parent bacterial plasmid creating a recombinant DNA molecule which can be propagated in bacteria. After cloning, the recombinant plasmid is further modified by introduction of the AGAT genetic sequence thereof into unique restriction sites of the viral portion of the plasmid. The modified viral portion of the recombinant plasmid is then excised from the parent bacterial plasmid, and used to inoculate the plant cells or plants.

Another method of introducing the gene encoding AGAT into plant cells is to infect a plant cell with *Agrobacterium tumefaciens* previously transformed with the gene. Under appropriate conditions known in the art, the transformed plant cells are grown to form shoots or roots, and develop further into plants.

Agrobacterium is a representative genus of the gram-negative family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes.

Heterologous genetic sequences such as the chimeric aadA gene can be introduced into appropriate plant cells, by means of the Ti plasmid of *Agrobacterium tumefaciens*. The Ti plasmid is transmitted to plant cells on infection by *Agrobacterium tumefaciens*, and is stably integrated into the plant genome. J. Schell, *Science* 237: 1176-1183, 1987.

Ti plasmids contain two regions essential for the production of transformed cells. One of these, named transferred DNA (T-DNA), is transferred to plant nuclei and induces tumor formation. The other, termed virulence region, is essential for the transfer of this T-DNA but is not itself transferred. The transferred DNA region, which transfers to the plant genome, can be increased in size by the insertion of the gene encoding AGAT without its ability to be transferred being affected. A modified Ti plasmid, in which the tumor-causing genes have been deleted, can be used as a vector for the transfer of the gene constructs of this invention into an appropriate plant cell.

Construction of recombinant Ti plasmids in general follows methods typically used with the more common bacterial vectors such as pBR322. Additional use can be made of accessory genetic elements sometimes found with the native plasmids and sometimes constructed from foreign sequences. These may include but are not limited to "shuttle vectors", Ruvkun and Ausubel, 1981, Nature 298:85-88, promoters, Lawton et al., 1987, Plant Mol. Biol. 9:314-324 and structural genes for antibiotic resistance as a selection factor, Fraley et al., *Proc. Nat. Acad. Sci.* 80:4803-4807, 1983.

All plant cells which can be transformed by Agrobacterium and from which whole plants can be regenerated from the transformed cells can be transformed according to the invention to produce transformed intact plants which contain and express the transferred gene encoding AGAT.

There are two common ways to transform plant cells with Agrobacterium:

(1) co-cultivation of Agrobacterium with cultured isolated protoplasts, or (2) transformation of intact cells or tissues with Agrobacterium.

Method (1) requires an established culture system that allows for the culturing protoplasts and subsequent plant regeneration from cultured protoplasts.

Method (2) requires (a) that the intact plant cells or tissues can be transformed by Agrobacterium and (b) that the transformed cells or tissues can be induced to regenerate into whole plants. In both method (1) and (2), both a T-DNA and a vir region are required for transformation, but only the T-DNA genetic region is incorporated into the plant nuclear DNA.

After transformation of the plant cell or plant, those plant cells or plants transformed by the Ti plasmid comprising the gene encoding AGAT can be selected by growing the plant cells on growth medium containing either spectinomycin or streptomycin.

After selecting the transformed cells by virtue of their ability to accumulate chlorophyll on the growth medium, one can confirm expression of the desired heterologous gene. Simple detection of RNA encoded by a cloned gene can be achieved by well known methods in the art, such as Northern blot hybridization, Maniatis. Isolation of the heterologously expressed gene product, if desired, can be accomplished by lysing the host cells and applying standard protein purification techniques with bioassays at each step until the product is purified sufficiently for identification on SDS polyacrylamide gels.

After determination of the presence and expression of the desired gene products, whole plant regeneration is desired. All plants from which protoplasts can be isolated and cultured to give whole regenerated plants can be transformed by the present invention so that whole plants are recovered which contain the transferred AGAT gene. Some suitable plants include, for example, species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersion, Nicotiana, Solanum, Petunia, Digitalis, Majorana, Cichorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum, and Datura.

It is known that practically all plants can be regenerated from cultured cells or tissues, including but not limited to all major species of sugarcane, sugar beet, cotton, fruit and other trees, legumes and vegetables. Limited knowledge presently exists on whether all of these plants can be transformed by Agrobacterium. Species which are a natural plant host for Agrobacterium may be transformable in vitro. Monocotyledonous plants, and in particular, cereals and grasses, are not natural hosts to Agrobacterium. Attempts to transform them using Agrobacterium have been unsuccessful until recently. Hooykas-Van Slogteren et al., Nature 311:763–764, 1984. Thee is growing evidence now that certain monocots can be transformed by Agrobacterium. Using novel experimental approaches that have now become available, cereal and grass species may now be transformed.

Additional plant genera that may be transformed by Agrobacterium include Ipomoea, Paasiflora, Cyclamen, Malus, Prunus, Rosa, Rubus, Populus, Santalum, Allium, Lilium, Narcissus, Ananas, Arachis, Phaseolus and Pisum.

Plant regeneration from cultured protoplasts is described in Evans et al., *Handbook of Plant Cell Cultures*, Vol. 1: (MacMillan Publishing Co. N.Y., 1983); and Vasil I.R. (ed.), *Cell Culture and Somatic Cell Genetics of Plants*, Acad. Press, Orlando, Vol. I, 1984, and Vol. III, 1986.

Means for regeneration vary from species to species of plants, but generally a suspension of transformed protoplasts containing copies of the gene encoding AGAT and other desired heterologous genes is first provided. Callus tissue is formed and shoots may be induced from callus and subsequently rooted. Alternatively, embryo formation can be induced from the protoplast suspension. These embryos germinate as natural embryos to form plants. The culture media will generally contain various amino acids and hormones, such as auxin and cytokinis. It is also advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

The mature plants, grown from the transformed plant cells, are selfed and non-segregating, homozygous transgenic plants are identified. The inbred plant produces seed containing the gene for both the AGAT enzyme and desired heterologous product. These seeds can be grown to produce plants that are resistant to streptomycin and spectinomycin as well as producing the desired expression product. For example, the antibiotic resistance of the transformed plants can be determined by growing them in the presence of the antibiotics.

The inbreds according to this invention can be used to develop hybrids or novel varieties embodying the desired traits. Such plants would be developed using traditional selection type breeding.

D. Definitions

The phrase "DNA sequence" refers to a single or double-stranded polymer of deoxyribonucleotide bases read from the 5' to the 3' end. It includes both self-replicating plasmids, infectious polymers of DNA and non-functional DNA.

The phrase "DNA segment" refers to a discrete portion of a DNA sequence that has a defined purpose or function. For example the AGAT encoding DNA is typically a part of a larger sequence. The DNA sequences encoding that AGAT enzyme are described as a segment of the entire sequence.

The phrase "gene product" refers to either the stable transcribed mRNA derived from a given gene or its translated polypeptide.

The term "promoter" refers to a region of DNA upstream from the structural gene and involved in recognition and binding RNA polymerase to initiate transcription.

The phrase "polyadenylation sequence" refers to any DNA sequence capable of promoting polyadenylation of m-RNA in eucaryotes. It should be noted that post-transcriptional modifications of this type do not necessarily conform to base complementarity and utilize enzymes different from RNA polymerases, e.g., polynucleotide phosphorylase.

The term "aminoglycoside 3''-adenyltransferase" includes the native and mutated forms of the prokaryote genes having the given functional capacity. It being further understood that polymorphism is likely and that minor allelic mutations both naturally occurring and deliberately induced are embraced by the term. Indeed, minor substitutions, deletions or additions to the primary amino acid sequence are possible and will have minimal impact upon the bioactivity of the enzyme. For example, glutamine and asparagine, aspartate and glutamate residues are often interchangeable.

The term "plant" includes whole plants, plant parts (e.g., leaves, stems, roots, seeds, etc.) and plant cells.

The phrase "suitable host" refers to a microorganism or cell that is compatible with a recombinant plasmid, DNA sequence or recombinant expression cassete and will permit the plasmid to replicate, to be incorporated into its genome, or to be expressed.

The following examples are provided by way of illustration and not by way of limitation. They should not be construed as limiting the claims embracing this invention.

EXAMPLES

Starting materials

The adenyl transferase gene, aadA, was obtained from Dean Taylor on the plasmid pDTP274, a higher copy number mutant derivative of plasmid pDTP270, Taylor and Cohen, *J. Bacteriol.* 137:92–104, 1979. The aadA gene was cloned as a 1.8 kb PvuII-HindIII fragment into SmaI-HindIII cut plasmid vector pUC118 to yield plasmid SP118.

Plants were transformed utilizing the *Agrobacterium tumefaciens* strain EHA101, Hood, et al., *Biotechnology* 2: 707–709, 1984 and the pZS97 binary plant transformation vector. The binary plant transformation vector pZS97 is similar to binary vector pGV941, Deblaere et al., *Methods in Enzymology* 153:277–292, 1987. It carries an engineered NPTII gene that confers kanamycin resistance to plants, the lacZ alpha peptide with the polylinker cloning sites from pUC19 for selection of clones with inserts on X-gal, and the beta lactamase gene that confers ampicillin resistance to *E. coli* and carbenicillin resistance to *A. tumefaciens*.

In the transformation experiments, wild-type *N. tabacum* cv. Petit Havana plants were used.

Mutagensis of aadA gene

The sequence of the aadA gene has been determined, Chinault et al., 1986, supra. An XbaI site was introduced into PsP118 3' to the aadA translation termination codon TAA byoligonucleotide mutagenesis as described by Harpster et al., *Mol. Gen. Genet.* 212:182–190, 1988. The wild-type sequence 5' ATAATGTCTAACAATTCGTTCA 3' was altered to 5' ATAATGTCTAGAAATTCGTTCA 3' to yield plasmid pPM19. The translation initiation codon of the aadA gene is contained in a BspHi site (TCATGA), and so that aadA coding sequence could be excised as a 793 bp BspHi-XbaI fragment from plasmid pPM19.

Expression plasmid constructs

Chimeric genes have been constructed for expression in plants by fusing the aadA coding sequence with a modified 35S promoter of cauliflower mosaic virus, the 5' untranslated leader sequence of the chlorophyll ab binding protein, and the Agrobacterium octopine synthase polyadenylation signals (pPM21), and the promoter region of the 2' (mannopine synthase) gene and the nopaline synthase polyadenylation signals of *Agrobacterium tumefaciens* T-DNA (pPM22). The chimeric genes have been introduced into the binary plant tranformation vector pZS97 to yield plasmids pPM24 and pPM25, respectively.

The steps of construction for pPM24 are shown schematically in FIG. 1, and outlined below. Plasmid pJJ3431 carries a 35S(J):Cab22L/beta-glucuronidase/ocs3' fusion. The 5' 35S(J):Cab22L, Harpster et al., 1988, supra and 3' ocs (octopine synthase) regions of pJJ3431 have been described, Gielen et al., 1984, EMBO J. 3:835–846. The 793 bp BspHI-XbaI fragment from plasmid pPM19 was ligated into the vector part of HcoI and XbaI digested plasmid pJJ3431 that resulted in a precise fusion of 35S(J):Cab22L with the aadA gene (pPM21). 35S(J):Cab22L/aadA/ocs was cut out from pPM21 as a 1.8 kb fragment, using the BglII (260 bp upstream of ATG) and HindIII (3' to ocs polyadenylation signal) sites and ligated into BamHI-HindIII digested binary plant transformation vector plasmid pZS97, yielding plasmid pPM24. In pPM24 the chimeric aadA gene is linked to an NPTII gene that confers kanamycin resistance to plants.

Steps of construction of pPM25 are shown schematically in FIG. 1, and outlined below. Plasmid pJJ3871 carries a 2'/beta-glucuronidase/nos3' fusion. In this construct the beta-glucuronidase gene is under the control of the Agrobacterium Ti-plasmid 2' promoter, Velten, et al., EMBO J. 3:2723–2730, 1984, and is 5' to the 260 bp TagI-ClaI fragment that contains the nopaline synthase (nos) polyadenylation signal, Depicker et al., 1982, supra. The beta-glucuronidase reading frame was excised with the NcoI and XbaI restriction endonucleases. The 793 bp BspHI-XbaI aadA fragment was ligated into the vector part of NcoI-XbaI cut pJJ3871, yielding plasmid pPM22. The 2'/aadA/nos construct was cut out from pPM22 as a 1.9 kb EcoRI-HindIII fragment, and ligated into EcoRI and HindIII digested binary plant transformation vector pZS97 to yield plasmid pPM25. In pPM25, as in pPM24, the chimeric aadA gene is linked to an NPTII gene that confers kanamycin resistance to plants (FIG. 1).

This permitted either direct selection for phenotypes conferred by the chimeric aadA gene, resistance to spectinomycin and streptomycin, or selection for kanamycin resistance and subsequent screening for spectinomycin resistance and/or streptomycin resistance.

Transfer of binary vector plasmids to Agrobacterium

Plasmids pPM24 and pPM25 have been introduced into the Agrobacterium strain EHA101 by triparental mating Hoekema, et al., *Nature* 303:179–180, 1984 using pRK2013 as a helper plasmid. Transconjugants were selected on minimal A sucrose medium containing 100 ug/ml carbenicillin.

Plant transformation

Protoplasts were prepared from leaves of *N. tabacum* plants grown in culture on MS salts and 3% sucrose, Maliga, P., 1984, in I.R. Vasil (Ed.) *Cell Culture and Somatic Cell Genetics in Plants,* Vol. I, pp. 552–562, Academic Press. Protoplast isolation and cocultivation were carried out according to Van Den Elzen, et al., *Plant Mol. Biol.* 5:149–154, 1985, except for the selection of antibiotic resistant cells. Protoplast-derived calli were selected for resistance to RMO medium containing spectinomycin dihydrochloride (100, 200, or 500 ug/ml), streptomycin sulphate (200 or 500 ug/ml), or both spectinomycin and streptomycin. Kanamycin selection was carried out in RMO medium containing 50 ug/ml kanamycin sulphate.

Formation of green calli in the plates indicated that aadA would confer resistance to either of the drugs alone, or to both (Table 1). Calli in the absence of Agrobacterium, however, were white. No significant difference in the frequency of resistant cones was found between samples transformed with pPM24 or pPM25. The frequency of transgenic clones was about the same when selecting for the linked kanamycin resistance marker (Table 1).

Plant regeneration from calli derived from protoplasts was carried out as described, Maliga, P., 1984, supra.

Leak disk transformation was carried out by cocultivation on RMO medium containing 50 ug/ml kanamycin sulphate, 100 ug/ml or 500 ug/ml spectinomycin dihydrochloride, 500 ug/ml streptomycin sulphate, or both spectinomycin (100 ug/ml) and streptomycin (500 ug/ml).

The same Agrobacterium strains carrying plasmids pPM24 and pPM25 were also used to select transgenic clones after leak disk cocultivation. Spectinomycin (100 ug/ml and 500 ug/ml, streptomycin (500 ug/ml) or the drugs applied together (spectinomycin, 100 ug/ml; streptomycin, 500 ug/ml) prevented greening of callus formed on leaf sections. Green callus with shoots, however, formed after co-cultivation with Agrobacterium.

The shoots were rooted in sterile culture in the absence of drugs, and their leaves were tested for resistance by formation of green callus on a selective RMO medium (100 ug/ml spectinomycin). Shoots were chosen so that they would represent an independent clone. Out of the 17 plants tested (8 and 9 pPM24 and pPM25 transgenics, respectively), al but one plant expressed resistance to spectinomycin.

The response of shoots was the same whether selected on spectinomycin, streptomycin, or both drugs. The plant that was sensitive to spectinomycin was also sensitive to kanamycin, so it probably regenerated from non-transformed, chimeric tissue. Kanamycin resistance was not expressed in an additional three clones. This may have been due to position effects, incomplete transfer, or deletions of the T-DNA, Jones et al., *Mol. Gen. Genet.* 207:478–485, 1987.

Plants have also been regenerated after selection for the linked kanamycin resistance marker. These plants were then screened for expression of spectinomycin resistance by the leaf assay, as discussed above. Out of 19 plants (6 and 13 pPM24 and pPM25 transgenics, respectively), all but two were resistant to spectinomycin. One of the spectinomycin-sensitive plants was also sensitive to kanamycin and was probably derived from chimeric tissue. The other plant was resistant to kanamycin. Lack of expression of the aadA gene in this plant, therefore, may have been due to position effects, incomplete transfer, or deletions of the T-DNA, as discussed above.

Seed progeny

Resistance phenotype of seedlings was determined by germinating surface-sterilized seedlings on MS salts, 1% glucose, Maliga, P., 1984, supra. The selective media contained 200 ug/ml of Kanamycin sulphate, 50 ug/ml spectinomycin dihydrochloride, 200 ug/ml streptomycin sulphate, or both 50 ug/ml spectinomycin dihydrochloride and 200 ug/ml streptomycin sulphate.

Seed progeny of regenerated plants was tested for the expression of resistance to spectinomycin and streptomycin. Seedlings were considered resistant when green, and sensitive when white on a selective medium. Spectinomycin resistance could be scored in the range of 50 ug/ml to 1,000 ug/ml; streptomycin resistance could be scored in the range of 200 ug/ml to 1,000 ug/ml (data not shown). Expression of resistance in seedlings correlated with expression of resistance in the leaf assays in all the 14 pPM24 transgenic lines tested. Phenotype conferred by the aadA gene was expressed in seedlings in 12 out of the 14 pPM25 clones that expressed spectinomycin resistance in a leaf assay.

Inheritance of the linked kanamycin resistance marker was also scored in the seed progeny. Expression of resistance in seedlings correlated with expression of resistance in the leaf assays.

Seed transmission data are given in Table 2 for clones in which aadA and NPTII sequences have been confirmed by Southern analysis.

Southern blot analysis

Leaf DNA has been prepared from plants expressing resistance to spectinomycin/streptomycin and to kanamycin, DNA was isolated and purified on CsCl density gradients, Thomashow, et al., *Cell* 19:729–739, 1980. High molecular weight plant DNA was digested by EcoRI and HindIII, electrophoresed in 07% agarose gels (5 ug/lane), and transferred to nitrocellulose. Hybridization was carried out at 42° C. in 50% formamide for 40 hours, Maniatis. pJJ1124, a pSP64 clone containing the BglII-SmaI fragment from transposon Tn5, Jones et al., 1987, supra, was used to make riboprobes for NPTII encoding DNA. pZS122, a pGEM-72f(+) clone containing the aadA encoding ClaI-XbaI fragment from pJJ4577 was used to make riboprobes for aadA encoding DNA. Plasmid pJJ4577 is identical to pPM21 except that the BspHI site has been converted to a ClaI site by oligonucleotide directed mutagenesis. The number of copies integrated per cell was calculated, assuming 9.7 pg DNA per nucleus in somatic cells of *N. tabacum*, Galbraith et al., *Science* 220:1049–1051, 1983.

Hybridization of aadA and NPTII probes confirmed transformation. The size of hybridizing EcoRI-HindIII fragment containing the aadA coding sequence was 1.8 kb and 1.9 kb in the transgenic pPM24 and pPM25 lines, respectively, as expected. Line 24–1000 contained only a larger hybridizing fragment. Probing in the same clone also revealed a rearranged NPTII coding sequence. Rearranged aadA sequences, in addition to predicted size copies, were present in clone 24-1. Based on copy number reconstruction, we estimate that the transgenic plants carry 2 to 5 copies of integrated intact aadA and NPTII genes.

In summary, resistance to spectinomycin and streptomycin has been conferred to *N. tabacum* cells after introduction of the chimeric aadA genes. Transgenic clones could be identified in protoplast culture, and in leaf disk culture after cocultivation with Agrobacterium carrying the chimeric aadA gene. Spectinomycin in culture was used for selection in the range of 100 to 500 ug/ml (Table 1). Streptomycin in culture was used for selection in the range of 200 to 500 ug/ml (Table 1). In seedlings spectinomycin resistance was scored in the range of 50 to 1,000 ug/ml (Table 2). Streptomycin resistance was a useful seedling marker in the 200 to 1,000 ug/ml range (Table 2). No difference in the level of resistance to spectinomycin or streptomycin was found between the pPM24 and pPM25 transgenic lines at the drug levels discussed above. Seedlings of pPM24, but not of the pPM25 line, however, were resistant to 2,000 ug/ml of spectinomycin (data not shown). This higher resistance level is expected since the 35S promoter is stronger than the 2' promoter, Harpster et al., *Mol. Gen. Genet.* 212:182–190, 1988.

TABLE 1

Transformation of *N. tabacum* protoplasts for resistance to spectinomycin, streptomycin and kanamycin[a].

| Plate | aadA | Sp | Sm | Sm/Sp | Km |
|---|---|---|---|---|---|
| 1. | — | 0%[e] | 0%[e] | 0%[e/e] | 0%[b] |
| 3. | — | 0%[c] | 0%[e] | 0%[e/c] | 0%[b] |
| 4. | — | 0%[e] | 0%[d] | 0%[d/e] | 0%[b] |
| 8. | pPM24 | 5%[d] | 9%[d] | 15%[d/d] | 2%[b] |
| 14. | pPM24 | 4%[e] | 6%[d] | 7%[d/e] | 3%[b] |
| 9. | pPM25 | 11%[d] | | 18%[d/d] | 22%[b] |

TABLE 2

Kanamycin, streptomycin and spectinomycin resistance in the seed progeny[a].

| Line[b] | G | Km[200] G/W | (R) | Sm[200] G/W | (R) | Sp[50] G/W | (R) | Sm[200]/Sp[50] G/W | (R) |
|---|---|---|---|---|---|---|---|---|---|
| 24-1 | 156 | 67/29 | (3:1) | 82/30 | (3:1) | 38/14 | (3:1) | 75/29 | (3:1) |
| 24-2 | 87 | 51/13 | (3:1) | 52/14 | (3:1) | 79/35 | (3:1) | | |
| 24-1000 | 126 | 43/10 | (3:1) | 76/8 | (15:1) | 89/6 | (15:1) | | |
| 25-1000 | 78 | 72/22 | (3:1) | 88/32 | (3:1) | 80/22 | (3:1) | 40/11 | (3:1) |
| 25-1007 | 46 | 57/17 | (3:1) | 38/14 | (3:1) | 43/9 | (3:1) | 62/15 | (3:1) |

[a]Seedlings have been germinated on a medium containing 200 ug/ml kanamycin (Km[200]), 200 ug/ml streptomycin (Sm[200]) or 50 ug/ml spectinomycin (Sp[50]). Resistant seedlings were green (G), sensitive seedlings were white (W) on the selective medium. Ratio (R) of resistant to sensitive seedlings is given in the selfed progeny. Segregation ratios do not deviate significantly from expected values ($p > 0.05$).

[b]Transgenic lines transformed by pPM24 and pPM25 constructs (construct encoded in first two digits), and were selected by resistance to spectinomycin (24-1, 24-2) or kanamycin (24-1000, 25-1000, 25-1007)

TABLE 1-continued

Transformation of *N. tabacum* protoplasts for resistance to spectinomycin, streptomycin and kanamycin[a].

| Plate | aadA | Sp | Sm | Sm/Sp | Km |
|---|---|---|---|---|---|
| 12. | pPM25 | | 7%[e] | 11%[e/c] | 24%[b] |

[a]Frequency of resistant colonies is given as percent of calli formed in the absence of selection pressure. Agrobacterium strains carried plasmids pPM24 or pPM25 with the chimeric aad A gene. Three weeks after initiating cocultivation cultures from individual plates were split. A fraction was plated in the absence of drugs to determine plating efficiency; equal amounts were plated into different selection media. Plates initially contained $5 \times 10^5$ protoplasts. Plating efficiency in the control cultures was about 0.05%. The selective media contained 50 (b), 100 (c), 200 (d), or 500 (e) ug/ml of spectinomycin (Sp), streptomycin (Sm) or kanamycin (Km).

What is claimed is:

1. An isolated DNA molecule encoding a DNA sequence comprising a recombinant expression cassette capable of conveying spectinomycin resistance in plants containing a DNA sequence encoding an enzyme having the activity of an aminoglycoside 3''-adenyltransferase originating from Shigella Sp.

2. A DNA sequence of claim 1 wherein the cassette further comprises a promoter selected from the group consisting of plant viral promoters and the 2' gene of the T-DNA of *Agrobacterium tumefaciens*.

* * * * *